United States Patent
Ristolainen et al.

(10) Patent No.: US 6,285,895 B1
(45) Date of Patent: Sep. 4, 2001

(54) MEASURING SENSOR FOR MONITORING CHARACTERISTICS OF A LIVING TISSUE

(75) Inventors: Kimmo Juhani Ristolainen; Ari Mauri Nenye, both of Helsinki (FI)

(73) Assignee: Instrumentarium Corp., Helsinki (FI)

(*) Notice: Subject to any disclaimer, the term of this patent is extended or adjusted under 35 U.S.C. 154(b) by 0 days.

(21) Appl. No.: 09/136,719

(22) Filed: Aug. 18, 1998

(30) Foreign Application Priority Data

Aug. 22, 1997 (FI) .......................................... 973454

(51) Int. Cl.$^7$ ........................................... A61B 5/00
(52) U.S. Cl. ......................... 600/323; 600/310; 600/344
(58) Field of Search .................................. 600/310, 311, 600/322, 323, 324, 326, 340, 344, 473, 476

(56) References Cited

U.S. PATENT DOCUMENTS

| 5,279,295 | 1/1994 | Martens et al. |
|---|---|---|
| 5,611,337 | 3/1997 | Bukta. |
| 5,817,010 | * 10/1998 | Hibl ..................................... 600/344 |

FOREIGN PATENT DOCUMENTS

| 41 42 234 | 6/1993 | (DE). |
|---|---|---|
| 197 03 220 | 7/1997 | (DE). |
| 0 568 380 | 11/1993 | (EP). |
| 716830 | 6/1996 | (EP). |
| 92/21281 | 5/1992 | (WO). |
| 96/00518 | 6/1995 | (WO). |

OTHER PUBLICATIONS

Hok Instrument Ab, SafeSat Fiberoptic Pulse Oximetry Sensor Brochure.

* cited by examiner

*Primary Examiner*—Eric F. Winakur

(57) ABSTRACT

The invention relates to a measuring sensor (10), comprising: detector legs (1, 2 movable to varying distances (H1...H2) from each other; detector elements (11) and possible emission elements (12) in the detector legs; pivoting means, the detector legs being tiltable (M) relative to each other around a pivoting axis (13) established thereby; operating legs (3, 4), each of which is attached to done detector leg and serves as an extension thereof; a spring element (7) between the operating legs for producing a compressive force (P2) between the detector legs, containing for example a finger which is non-invasively measured with the measuring sensor for some characteristic. The spring element (7) consists of an elastomer material and a solid component, extending from the first operating leg (3) to the second operating leg (4). In addition, the spring element is in gripping contact with both operating legs (3 and 4) over such a length (L2) which is located substantially within a total length (L1) between the surrounding of said axis line (13) and outer ends (15) of the operating legs.

54 Claims, 3 Drawing Sheets

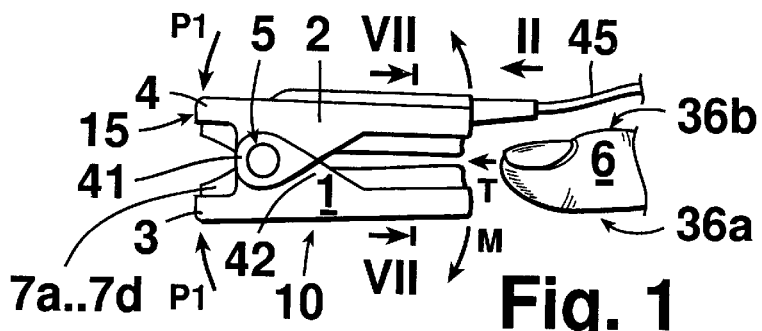
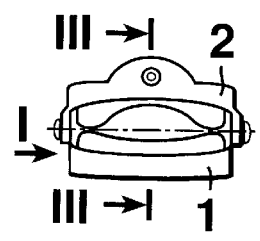
Fig. 1    Fig. 2
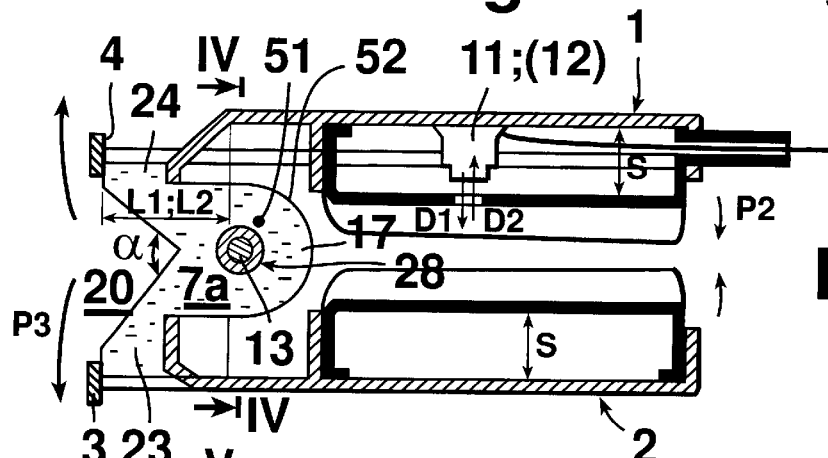
Fig. 3
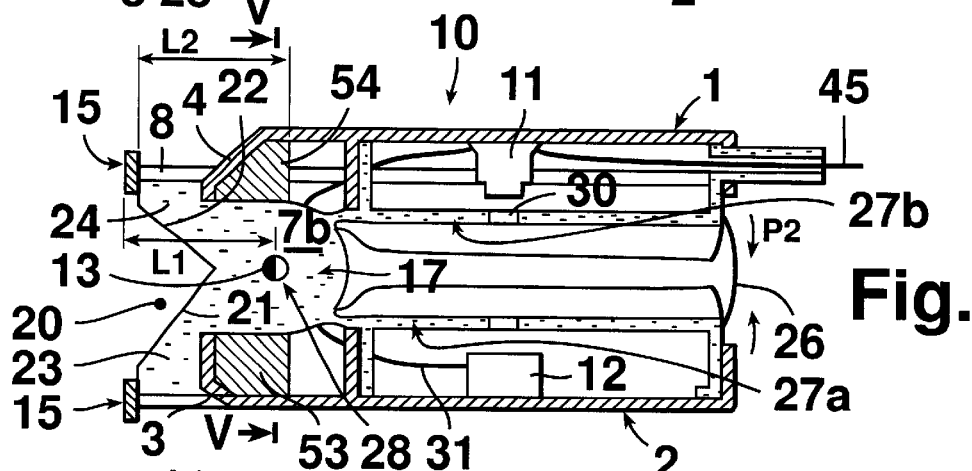
Fig. 4
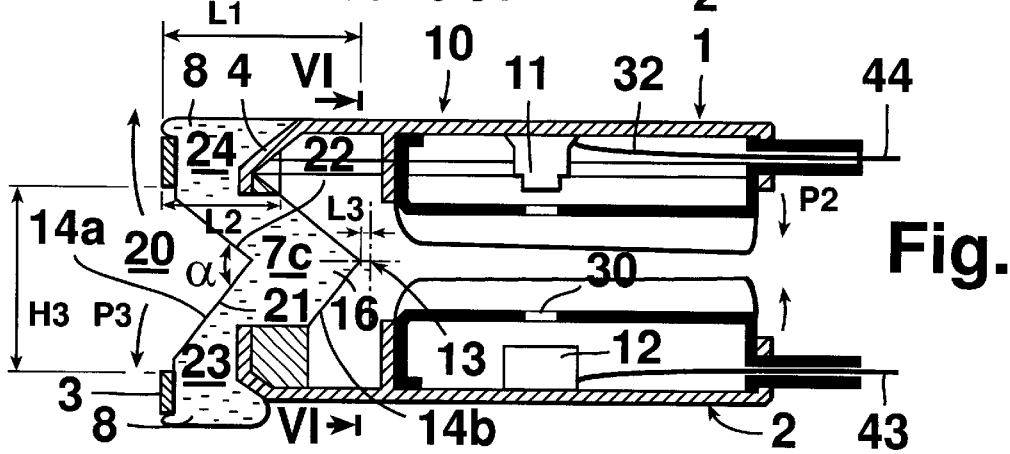
Fig. 5

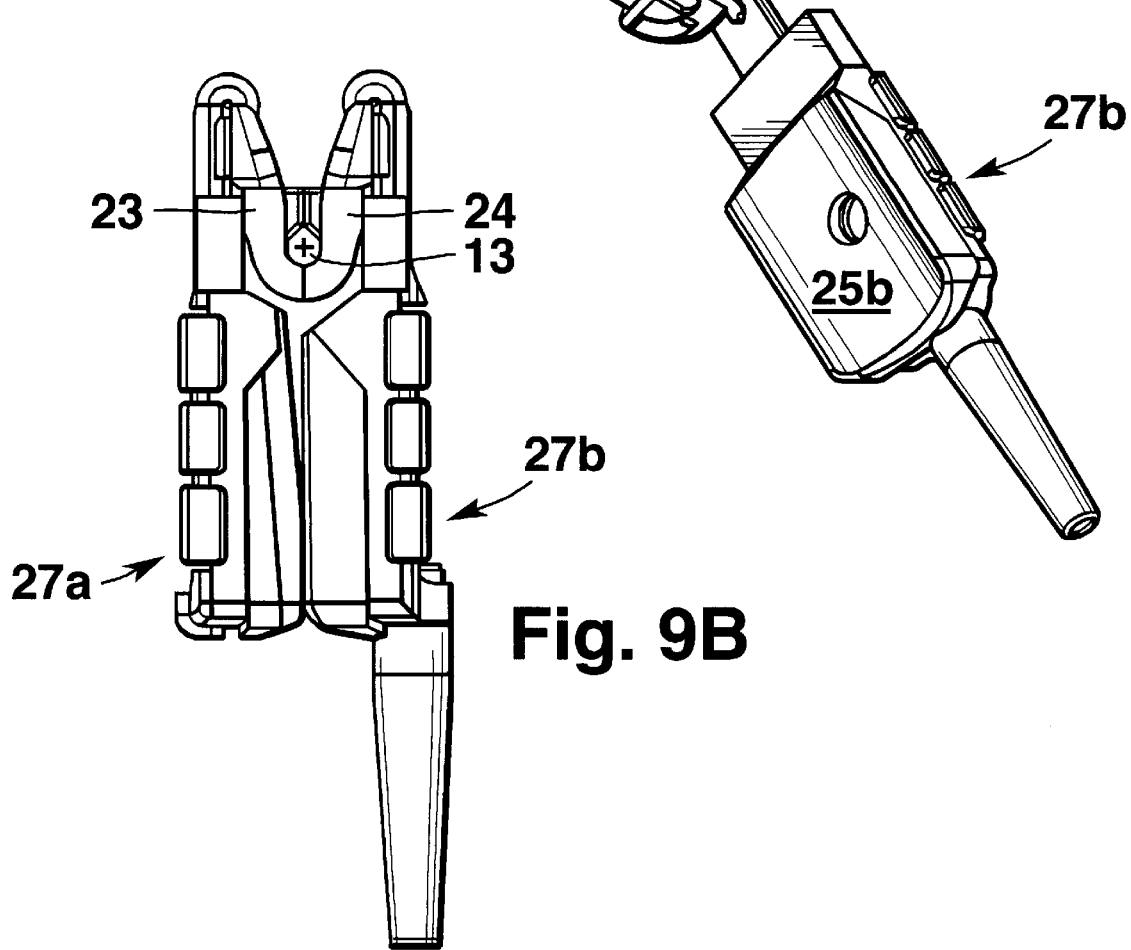

MEASURING SENSOR FOR MONITORING CHARACTERISTICS OF A LIVING TISSUE

BACKGROUND OF THE INVENTION

The present invention relates to a measuring sensor, comprising at least two rigid detector legs movable to varying distances from each other; detector elements and possible emission elements on one or both legs of the measuring sensor; pivoting means, the detector legs being tiltable relative to each other around a pivot axis line established thereby; at least two rigid operating legs, each being attached to one detector leg and, as an extension thereof, extending therefrom beyond the pivot axis line; and a spring element between the operating legs for producing a compressive force between the detector legs containing a piece of living tissue having one or a few of tissue dependent characteristics measured in a non-invasive manner by means of the measuring sensor, and said spring element being composed of an elastomer material. The invention relates also to the use of such a measuring sensor.

A typical application for the above-described type apparatus is currently a pulseoximetry sensor, but it is also possible to apply a similar type of measuring sensor for investigating or measuring some other characteristic of a living tissue, whereby the detectors and possible emitting sources must of course be chosen in consistency with the characteristic to be measured. Pulseoximeters are used e.g. for measuring the blood oxygen saturation of a patient non-invasively and continuously. The term non-invasive refers to the fact that no physical means are used to penetrate under the patient's skin, but the measurement is carried out by means of radiation and, aside from that, the action takes place externally of the body. Such monitoring of blood oxygen saturation is presently quite commonplace and one of the monitoring parameters required in many conditions. The measurement is optical and based on different absorption characteristics of red and infrared light in blood hemoglobin. At present, the pulseoximetry sensors have normally two light sources, typically radiation emitting diodes (LED), and one detector, said radiation sources being operated alternately in a synchronized fashion. In either case, the radiation sources and detectors can be first of all included in the sensor itself in the proximity of an object to be measured and from the sensor extend electrical cables to a surveillance monitor. However, the above-described conventional solution cannot be used, for example, during the operation of more and more popular magnetic imaging of a patient or some other powerful electromagnetic source. In these conditions, for example the electrical cable of a sensor would function as an antenna and all metal components in the measuring sensor or, generally defined, the components affecting a magnetic field and/or electrically conducting components interfere with the magnetic imaging apparatus and distort the imaging result, i.e. all such components in a measuring sensor cause trouble and ruin the magnetic images. Thus, the pulseoximetry sensors applicable in a magnetic imaging environment are typically designed by using fiberoptics. Hence, the light sources and the detector or detectors are located remotely from the actual area of imaging, such as on the housing of a surveillance monitor or in some other corresponding location. The light power is carried to and from a measuring location by means of a fiberoptic cable, comprising in practice a bundle of fibers constituted by a multitude of thin optical fibers and having a diameter which is typically 1–3 mm.

The above type measuring sensors, used for example in pulseoximetry, are generally composed of rigid detector legs and operating legs as extensions thereof, the detector legs and operating legs having a junction which is provided with pivoting means, such as a sort of link mechanisms or the like, whereby the operating legs can be pressed for spreading the detector legs from each other, the piece of living tissue to be measured, such as a finger, a toe, or an ear, being thus insertable between the detector legs. In addition to this, the measuring sensor must include some type of a spring element for maintaining the detector legs pressed against a piece of living tissue during a measuring process. The publication EP-0,716,830 A1 discloses a measuring sensor which is only provided with detector legs, but not with operating legs, and which mentions a spring element integral with the structure, the publication containing, however, no specific description in terms of the material, function, design, or other details of such element. The publication U.S. Pat. No. 5,279,295 describes one of the most common measuring sensor designs, wherein the detector legs can be pressed against a member of living tissue, such as a finger, by means of a rubber band extending around the detector legs. This is a very awkward solution and requires in a practical situation the fitter of a measuring sensor to have nimble fingers and to perform a considerable amount of all sorts of nibbling. Moreover, such a rubber band is an item that comes off and is lost easily, rendering the measuring sensor useless. The publications WO 92/21281 and WO 96/00518 introduce measuring sensors which include not only detector legs but also at least some kind of operating legs for pivoting the detector legs around a physical axle or a virtual axis. These measuring sensors employ metal springs, especially a clip type of spring, for producing a compressive force between the measuring sensor and a finger serving as the object to be measured. As pointed out above, all metal components present in a measuring sensor interfere at least in an environment of magnetic imaging with the production of a satisfactory magnetic image. In many other applications as well, it is advisable that the measuring sensor not be provided at least with any considerable numbers of metal components.

In addition to the above-described solutions, a company called HÖK INSTRUMENT AB has introduced to the market a pulseoximetry sensor entitled "SafeSAT". The sensor is intended to be attached to a finger for measuring the oxygen saturation of blood. This measuring sensor is provided with two detector legs and, as an extension thereof, rigidly connected operating legs, the junction area of said leg members being provided with a simple mechanical hinge axle. As for the detector legs, the structure is relatively conventional, comprising soft pads coming into contact with a finger and radiation emitting components in one leg and detecting components in the other leg, which are by way of optical cables in communication with actual detectors and radiation sources located externally of the measuring sensor. The above-discussed spring force is established by means of two lengths cut off an elastic tube of silicone rubber and fitted between the operating legs, the axial lines of said tubes being parallel to the detector legs and to said pivoting axis of the operating legs. Hence, these lengths of silicone tube are perpendicular to the moving direction of the detector legs. The operating legs are provided with inner surfaces facing each other, which are completely smooth and flat and the lengths of silicone rubber tube are bonded securely to these surfaces. The lengths of silicone rubber tube are by no means attached to each other, but the immobilization thereof is only achieved by the bonding between the silicone rubber tube and the inner surface of the operating legs. The bonding between elastic silicone rubber and some other type of plastics is very difficult to achieve and requires a plurality of working steps, in spite of which the bonding result is always quite unreliable. Thus, many of these sensors become useless even during the first time of use, in other words, really, it cannot be used used even for the first time as the bonding between a silicone rubber tube and an operating leg unfastens, the compression between the detector legs and the finger becoming unreliable or failing completely. Furthermore, in this marketed solution, the optical cables are brought out of the measuring sensor through cut-outs in the silicone rubber tubes, the making of said cut-outs requiring manual work or at least a separate working phase. This also adds to the costs of this solution. Yet another drawback in this marketed solution is the large number of various cut-outs, recesses, and the like, which are required by silicone rubber tubes and optical cables running therethrough and which easily accumulate dirt. Thus, the hygiene, or rather sterility, of this measuring sensor marketed by HÖK INSTRUMENT AB is highly questionable, particularly in continuous use. In fact, it can be argued that, for example in surgical conditions, such a non-hygienic or poorly sterilizable instrument should not be used at all.

The publication U.S. Pat. No. 5,611,337 describes a pulseoximetry sensor attachable to an ear lobe, comprising a one-piece injection molded support structure provided with two legs set on the opposite sides of an ear lobe. One leg is provided with a measuring assembly consisting of a radiation source and a detector. The described structure includes a web, which is provided with a rib projecting therefrom in the direction of a plane parallel to the legs and arranged either on the web surface facing the legs or on the web surface facing away from the legs. According to the cited publication, the legs press against the ear lobe as a result of the elasticity of this rib projecting from the web. Admittedly, this described construction is smooth in terms of its outer surfaces and, thus, the cleanliness and sterility of such a pulseoximetry sensor are readily sustainable. However, the construction has also drawbacks. First of all, since the inter-leg compressive force is produced by means of a rib extending in the moving direction of the legs, which in one embodiment constitutes a spring based solely on tensile stress or in another embodiment a spring based solely on compression stress, the inter-leg force depends very definitely on a distance between the legs. A consequence of this is that the thickness of a measured object must always be quite accurately the same, since an object thinner than usual results in a very weak compression and, thus, in a risk of the entire sensor falling off, while an object thicker than usual results in an excessively strong compression and, thus, at least in discomfort for a patient but possibly also in a reduced blood circulation in the area of measurement and possibly thereby in an incorrect measuring result. This sensitivity to excessively weal and excessively strong compression is further enhanced by the shortness of the legs. In the depicted structure, the legs cannot be expanded to surpass the length or width of the measuring assembly, since this results in the entire construction becoming far too floppy and inexact, the measuring elements being able to shift into uncontrollable positions. In addition, the sensor legs have such a surface contour that under no circumstances is the depicted device able to hold its position on top of a narrow and convex-shaped measuring object, such as a finger or a toe, but will be slipping off. Thus, the measuring sensor shown in the cited publication does not have a very good range of utility.

BRIEF SUMMARY OF THE INVENTION

A primary object of the invention is first of all to provide such a general structure for a measuring sensor, which facilitates the use of the same measuring sensor at measuring objects of various sizes in such a manner that regardless of the size of a measuring object the measuring sensor retains its position reliably and, at the same time, its compression is as independent as possible of the thickness of a measuring object and, in addition, the compressive force must generally be as light as possible. The primary objects of the invention encompass the construction of such a general structure or assembly that the measuring sensor retains its position even on a narrow member of the body, such as an appropriate finger or toe despite the possible movement or twitching thereof or slight bumps on the measuring sensor. Another object of the invention is such a general structure for a spring element which, by remodelling the spring element, can be attached to various sensor housing structures, such as a finger sensor, an ear sensor, or a nasal sensor. Hence, an object of the invention is to provide at least an elastic instrument for a measuring sensor, comprising detector legs, operating legs, and pivoting means in the junction area thereof, which elastic instrument, first of all, by no means interferes with a signal even in a magnet imaging environment and would guarantee good hygiene and good sterility for a measuring sensor for example for operating room conditions. A second object of the invention is the above-type of elastic instrument, whose immobilization on a measuring sensor would be as secure as possible and whose attachment to a measuring instrument would not require labour intensive or precision demanding actions, such as bondings or the like. A third object of the invention is the above-type of elastic instrument in a measuring sensor, which could be manufactured speedily, simply, and cost-effectively. A fourth object of the invention is the above-type of elastic instrument, which is structurally such that a desired spring force between the detector legs is precisely designable and dimensionable and also the target figures set in practical production conditions will be precisely achieved. A fifth object of the invention is the above-described type of elastic instrument, which, if possible, would be structurally such that in a measuring sensor all elastic components could be manufactured from as few separate components as possible, which also contributes to structural sterility and economy in terms of manufacturing costs. Yet another object of the invention is at least a non-invasive measuring sensor constructed as described above, whose positioning on a measuring object would be quick, simple, and reliable.

The above-discussed drawbacks can be eliminated and the above-defined objects can be achieved by means of an elastic instrument of the invention, which is characterized by what is set forth in the characterizing clause of claim 1, as well as by the use of this measuring sensor, which is characterized by what is set forth in the characterizing clause of claim 12.

The most essential benefits gained by the invention include the extremely simple construction of a non-invasive measuring sensor and especially that of its elastic instruments, particularly a spring element, the low manufacturing and assembly costs, readily obtainable high sterility, and the fact that, under no circumstances, does the elastic instrument present in a measuring sensor cause magnetic or electric interferences with other equipment in use, such as magnetic imaging equipment. Other essential benefits of the invention include the versatility of the measuring sensor in terms of measuring objects, the same measuring sensor being suitable for oxygen saturation measuring at least from nearly any finger, toe, nostril, or ear of almost any patient. This advantage of high versatility can be appreciated from the fact that, for one reason or another, a patient may be missing any given one of these mentioned organs completely or it may be otherwise unfit for measurement. The basic structure of the invention, which consists of rigid detector legs tiltable relative to each other around a pivoting axis, as well as of a special spring element made possible by this basic structure allow for a long elasticity range between the detector legs while the compressive force applied to a tissue to be measured changes only slightly. A further advantage is that, in the measuring sensor of the invention, wherein the detector legs have a relatively large area starting from the common pivot axis line thereof, the padding on the inner surfaces thereof can be designed to facilitate the attachment to a measuring object, whereby the compressive force existing between the detector legs can be insignificant.

BRIEF DESCRIPTION OF THE SEVERAL VIEWS OF THE DRAWING

The invention will now be described in more detail with reference made to the accompanying drawings.

FIG. 1 shows a measuring sensor of the invention from outside in a lateral view from a direction 1 in FIG. 2, as well as a piece of living tissue, in this case a finger, prior to inserting it in a direction T in the measuring sensor between its detector legs.

FIG. 2 shows the measuring sensor of FIG. 1 from outside in an end view from a direction II in FIG. 1. The measuring sensor is shown in a position established by the compression of a spring element without a piece of living tissue.

FIG. 3 shows a longitudinal section of one preferred embodiment of the invention in a lengthwise section along a plane III—III in FIG. 2. The measuring sensor is shown in a position established by a spring element without a piece of living tissue.

FIG. 4 shows a second embodiment for a measuring sensor of the invention in a lengthwise section in the same view as FIG. 3 along the plane III—III in FIG. 2. The measuring sensor is shown in a position established by a spring element without a piece of living tissue.

FIG. 5 shows a third embodiment for a measuring sensor of the invention in a lengthwise section in the same view as FIGS. 3 and 4 along the plane III—III in FIG. 2. The measuring sensor is shown in a position established by a spring element without a piece of living tissue.

FIG. 9A shows a structural component according to a special embodiment for a measuring sensor of the invention, which constitutes both a spring element and a cushion or a jacket coming into contact with a tissue to be measured and which consists of a single component, in an extended and axonometric view.

FIG. 9B shows the single-piece spring element-cushion-unit of FIG. 9A, folded to a position assumed thereby inside a measuring sensor in an operative condition, in the same view as in FIG. 4. The embodiment is analogous to that of FIG. 4, but different in terms of details.

DETAILED DESCRIPTION OF THE INVENTION

Figure 6:
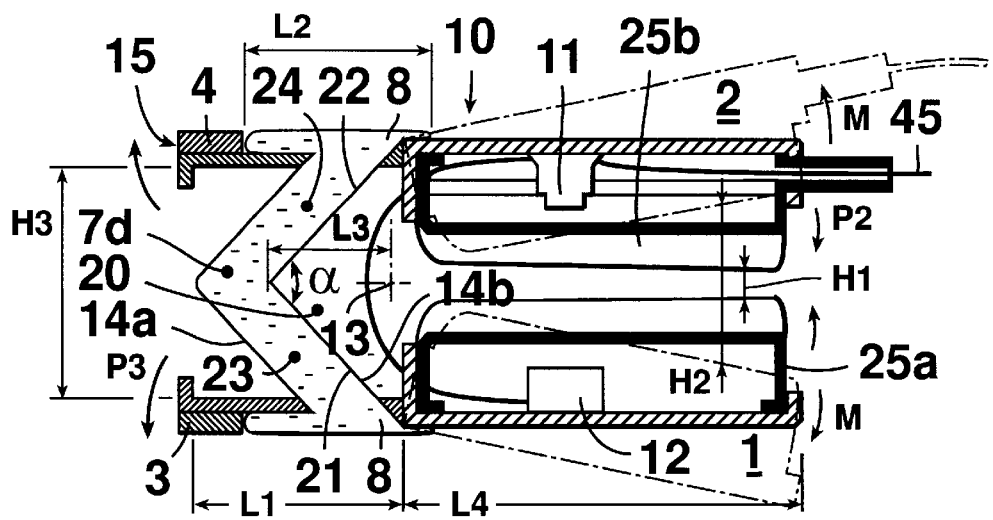
FIG. 6 shows a fourth embodiment for a measuring sensor of the invention in a lengthwise section in the same view as FIGS. 3, 4, and 5 along the plane III—III in FIG. 2. The figure shows in dashed lines the positions of detector legs in an extended position, which enables the insertion of a finger, a toe, an ear lobe, a septum nasi, or some other piece of living tissue between the detector legs, and in solid lines a measuring sensor in a position established by the compression of a spring element without a piece of living tissue.

Particularly FIGS. 1 and 2, but also FIGS. 3–6, illustrate the general features of a measuring sensor 10 of the invention as well as the features of an elastic instrument connected therewith. First of all, the measuring sensor 10 comprises at least two rigid detector legs 1 and 2 movable to unequal or variable distances H1→H2 from each other,. as shown in FIG. 6 in dashed lines and solid lines, respectively. Thus, these. detector legs are made of a rigid, i.e. hard and strong material, hence being substantially different from the materials of both an spring means and a cushion or jacket 25a, 25b coming into contact with a measuring object, the latter being described hereinafter. Of course, the material of the detector legs may not disturb e.g. magnetic imaging and, thus, the suitable material can be an appropriate plastics or reinforced plastic material. These unequal distances H1 . . . H2 are established by pressing operating legs 3 and 4 towards each other with a force P1, resulting in a reverse moment M which urges the detector legs to move from the position H1 closer to each other to the position H2 further away from each other. In this position H2, a piece of living tissue 6, such as a finger, is insertable in between the detector legs 1 and 2. The above-mentioned operating legs 3 and 4 are also stiff/rigid and each of those is attached at any given time to one of the detector legs 1, 2 or serves as an extension thereof, extending beyond a pivoting axis 13 over to the opposite side in relation to the detector legs 1 and 2. In this case, the operating leg 3 is directly an extension of the detector leg 1, providing an approximately straight portion, and the operating leg 4 is an extension of the detector leg 2, providing a respective, approximately straight portion. It is obvious that the operating leg and the detector leg attached thereto may also constitute a bend or an angle relative to each other, not shown in the figures. Neither is there anything to prevent the operating leg 4 from being formed as an extension of the detector leg 1 and the operating leg 3 as an extension of the detector leg 2, whereby these legs extend crosswise, other than in the figures, in which they run substantially parallel to each other. Preferably, the detector leg and a respective operating leg are connected to each other rigidly or can be made in a single piece, but it is also conceivable to have a somewhat flexible joint therebetween. At least the detector legs, but usually the detector legs and operating legs together, constitute an actual housing or a body for a measuring sensor of the invention, which uses its rigidity to retain the sensor shape, creates an axis line between the detector legs, and to which are connected other components of the invention. In order to provide the relatively facing sides of the detector legs with cushions or jackets 25a, 25b, having a sufficiently large area and, if necessary, matching inversely/negatively the shape of the outer surface of a measuring object, it is appropriate to design the detector legs of the housing body to have a sufficient length and width, thus also making use of the above-mentioned rigidity of the detector legs and possibly also the operating legs for developing a robust and precisely functioning measuring sensor. Hence, the detector legs have a length L4 from the axis line 13, as measured in a direction perpendicular to the axis line, which is at least 20 mm, but preferably at least 25 mm, and typically within the range of 30 mm–40 mm. The detector legs have widths W1 in the direction of the axis line 13d which are at least 10 mm, but preferably at least 15 mm, and typically within the range of 20 mm–25 mm. Thus, the detector leg 1 or 2 or the detector legs and, at the same time, at least one of the jackets 25a or 25b have a width which matches the width or thickness of a finger, a toe, or some other narrow and convex extremity of the body serving as an object of measurement. Especially, the sufficient width W1 facilitates making the sensor shape compatible with the relatively narrow and very convex outer shape of e.g. a finger or a toe. Thus, the detector legs have a length and a width whose ratio W1–L4 is within the range of 1:0,7–1:3, preferably within the range of 1:1,2–1:2,2, and typically within the range of 1:1,5–1:1.9.

Figure 7A:
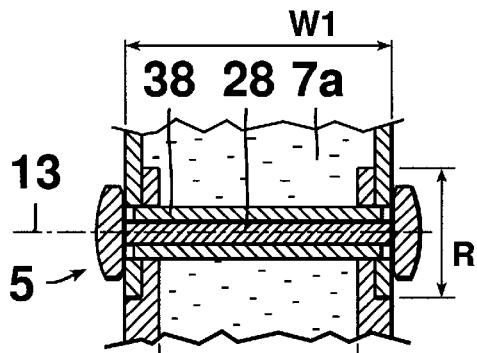
FIG. 7A shows a measuring sensor of the invention in cross-section along a plane IV—IV in FIG. 3.
Figure 7B:
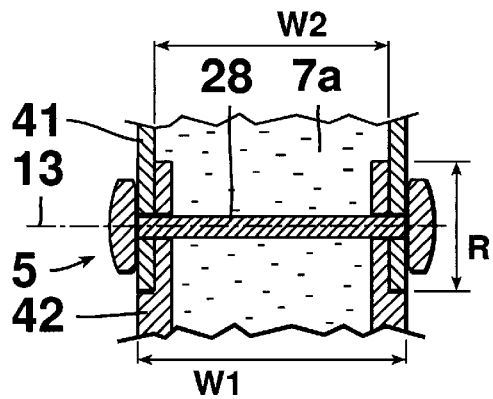
FIG. 7B shows a measuring sensor of the invention in cross-section along a plane V—V in FIG. 4.
Figure 7C:
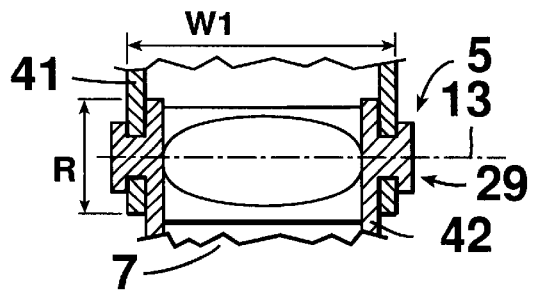
FIG. 7C shows a measuring sensor of the invention in cross-section along a plane VI—VI in FIG. 5.
Figure 8:
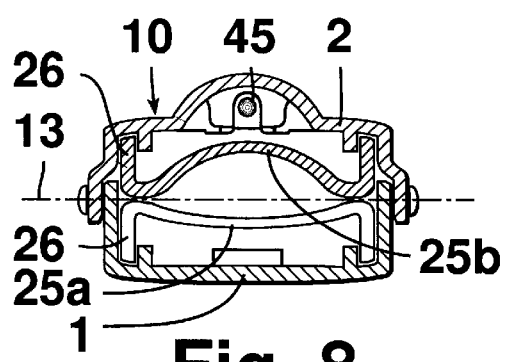
FIG. 8 shows a measuring sensor of the invention in cross-section along a plane VII—VII in FIG. 1.

In any case, the first detector leg-operating leg-unit 1, 3 is connected to the second detector leg-operating leg-unit 2, 4 by means of pivoting elements 5, which constitute the pivoting axis 13 around which the detector legs are tiltable M relative to each other by means of the operating legs. This pivoting axis 13 can be an axis line established by an actual real axle, as depicted in FIGS. 7A and 7B, or an apparent pivoting axis line 13, as shown in FIG. 7C. In theoretical sense, the pivoting axis 13 can be established entirely without the pivoting elements shown in the figures, but in this case the mobility P1→M of the measuring sensor to practical conditions is possibly too indefinite. In the illustrated case, wherein the detector legs and operating legs constitute approximately linear extensions to each other, the pivoting elements 5 are arranged within an overlapping area R of projections 41 and 42 extending towards each other and formed at the points of convergence of these legs, as conceivable by means of FIG. 1 and FIGS. 7A, 7B, and 7C.

Between the operating legs 3 and 4, the elastic instruments constitute a spring element 7 which, as a result of a moment acting around the pivot axis line 13, produces a compressive force P2 between the detector legs whenever the piece 6 of living tissue is present, the measuring sensor being used for non-invasively measuring one or more characteristics thereof. In this specification, the spring element is generally designated with reference numeral 7 whenever it is not necessary to specify the type of a spring element, but reference is made to any spring element 7 of the invention, representing various embodiments. If necessary, it is possible to use specified reference numerals 7a, 7b, etc. This spring element 7 consists of an elastomeric material, i.e. a material which is by no means metal but, instead, some synthetic polymer or natural polymer or plastics, having a molecular structure which provides it with elastic resilient properties, corresponding to the properties of a spring at the operating temperature. According to present understanding, the specified type of and/or illustrated spring elements develop their spring force at least to some degree and possibly to a substantial degree the way of a bending spring, i.e. they are not purely compression springs or tension springs or torsion springs. In any case, the force P2 created by a spring element of the invention between the detector legs 1, 2 remains within desired limits over the mobility range M required for the detector legs, the extent of said range depending on the thickness of fingers and/or toes and possibly ears existing among a group of patients.

In addition to this, one or both detector legs are provided with detector elements 11 and possible emission elements 12. The terms detector element and emission element are intended to refer to each of the possible alternatives, one of which has the actual actuator included in the measuring sensor 10 and the other has it mounted on the end of some conductor at a distance from the presently discussed measuring sensor 10. FIG. 3 illustrates basically two different alternatives. First of all, the first detector leg 1 can include only a detector element 11 for measuring radiation or a field or some other characteristic emitted by a living tissue by itself or for some reason independent of the measuring sensor. In a second alternative, the first detector leg 1 is provided with both emission elements 12 and detector elements 11, whereby this emission element-detector element-pair 11, 12 transmits to the piece of tissue 6 to be examined a desired type of radiation or some other signal and receives the same by means of the reflection caused by the piece of tissue 6. This purpose is served by a more or less integrated component 11+12, which contains both a detector element 11 and an emission element 12 as a single aggregate component. Of course, it is also possible to employ separate and e.g. side-by-side mounted detector elements and emission elements. If using e.g. a plurality of measuring wavelengths, all sub-components can be either integrated as a single aggregate component or partially integrated or entirely separate components. For example, it is possible to compile detector element pairs for measuring two or more wavelength bands and/or emission element pairs for emitting two or more wavelength bands or, optionally, emission element-detector element-pairs, wherein these two components process the same wavelength band. In the case that the active detectors and possible active emitters are remote from the measuring sensor 10, e.g. by way of optical cables, the integration does not bear major significance. FIGS. 4–6 illustrate the most commonly applied mode of operation, wherein the detector element 11 and the emission element 12 are included in the separate detector legs 1 and 2 of the measuring sensor 10. Thus, the piece of living tissue 6 placed between these detector legs 1, 2 will be penetrated by radiation transmitted by the emission element 12 or by some other signal and the variation caused by the piece of living tissue in this signal is measured by means of the detector element 11. The only difference between the embodiment of FIG. 4 and that of FIGS. 5 and 6 is that, in FIG. 5, a cable 43 of the emission element 12 is extended out of the measuring sensor 10 apart from a cable 44 of the detector element 11. On the other hand, in the case of FIGS. 4 and 6, both of these cables are integrated as a single cable 45. The presently discussed measuring sensor of the invention can be preferably used as a pulseoximetry sensor, but also for other equivalent or different measurements by selecting detectors and possible emitting elements in accordance with varying physical or chemical quantities.

According to the invention, a spring element 7a–7d, constituting a part of the spring instrument, comprises a substantially continuous or solid component extending from the first operating leg 3 to the second operating leg 4. The above-mentioned continuity refers preferably to the fact that there are no interruptions, in other words the spring element 7a–7d is preferably constituted by a single member between the first operating leg 3 and the second operating leg 4. There is nothing as such to prevent this solid component from being compiled by combining various materials or elements of various shapes together. Thus, this spring element 7a–7d may comprise a structure, having a surface which is tight, typically at least liquid tight and possibly also gas tight, and having an interior which can be porous. Such components, having a varying structure in the thickness direction, in this case the spring elements 7a–7d, can be manufactured by several conventional or novel techniques and, thus, those are not described here in more detail. As an example, it can just be mentioned that the spring element 7 could have an interior consisting of a foam-like material 51 and a housing of a dense layer 52, which materials can consist of either the same polymer or different polymers. It is of course possible to compile the spring element 7a–7d by bonding, not shown in the figures, from two or more components, but this is not a preferred embodiment due to the problems associated with bonding, as described earlier in this application. Thus, the most preferred embodiment, at least at the time this application is written, is that the spring element 7a–7d be compiled by a suitable molding technique or some other manufacturing technique, such as cutting and coating, into a substantially uninterrupted solid component, the continuity existing at least between the operating legs 3, 4. Furthermore, according to the invention, this spring element 7a–7d has a shape causing gripping with at least one of two pivoting legs 3 or 4, but preferably with both operating legs 3 and 4, over some such length L2 which lies within a total length L1 between the surroundings of said axis line 13 and outer ends 15 of the operating legs. This shape-based gripping refers to the fact that the spring element 7a–7d retains its position explicitly by virtue of the conforming or matching shapes between the operating legs 3, 4 and the spring element 7a–7d itself, instead of using adhesive or some other such method. This conformity of shapes can be based either on a clamping achieved by means of ends 8 of the spring element 7 and the operating legs 3 and 4, as illustrated very clearly in FIGS. 5 and 6, wherein the spring element ends 8 pass with a broader end through apertures in the operating legs or by means of a shaft 28 extending through the spring element 7a–7d, as shown in FIGS. 3 and 4 and 7A and 7B, respectively. Thus, the spring element ends include outside and inside the operating leg, in line with passage apertures present in the operating legs, portions that are broader than this aperture for preventing a passage of the spring element end 8 through the operating leg aperture in either direction, the spring element ends thus being locked to the operating legs by virtue of the shape thereof. In principle, it is also conceivable to use a reversed design, whereby the operating legs would be provided with sizable recesses which would accommodate the end expansions of a thin spring element. It should also be noted in this context that, in the conceptions of this specification, the spring elements 7 are also in a gripping contact based on their shape with e.g. portions 53 and 54 of the operating legs 3, 4 in FIG. 4, even if such portions were not made of a solid or continuous material but, instead, even provided with apertures or consisting of ribs, such as ribs extending in the direction of an image plane. In this case, the spring element is nevertheless in contact against a covering surface constituted by the outermost points of such portions 53, 54 together. This must be considered a shape-matching contact although, in this case, the portions 53, 54 do not achieve a gripping, but obviously otherwise contribute to the immobility and desired action of a spring element. Optionally, the spring element may of course extend into slots between the above-described apertures and/or ribs.

According to the invention, the elastomer-material spring element 7 of the invention can be designed in a plurality of ways. First of all, the spring element 7c, 7d may extend from the direction of the outer ends 15 of the operating legs maximally to said axis line 13, or may fall short of it by a length L3, as depicted in FIGS. 5 and 6. Thus, in terms of at least one, and preferably both of its outer surfaces substantially parallel to the axis line, in other words, in terms of its outer surfaces 14a, 14b lying in a plane perpendicular to the axis line 13, the spring element, in the direction of the axis line, is either concave, as shown in FIG. 6 in reference to the spring element 7d, or convex, as shown in FIG. 5 in reference to the spring element 7d. In these cases, the spring element 7c, 7d is not in a direct contact with the axial line 13, but this axial line 13 is constituted by means of a different mechanism, which will be discussed later in this specification.

Unlike what is described above, the spring element 7a, 7b may extend to the area of said axis line 13 and particularly around this axial line, as depicted in FIGS. 3 and 4. In this case, the spring element 7a, 7b includes projections 23, 24, corresponding to the directions of the operating legs 3, 4 and, as seen from the axis line 13, directed towards the ends 15 of the operating legs. In a preferred embodiment, a gap 20 between these projections 23, 24 in FIGS. 3 and 4 and, respectively, a gap 20 between the projections in FIGS. 5 and 6 are at least for the most part open to surrounding atmosphere, in other words, the question is about an aperture, which creates an angle formed by the spring element 7 and which is open to deformation. In theory, it is possible to close the gap 20, i.e. the aperture between the spring element projections 23, 24, by means of an elastic film, which extends from the flanks of the first projection 23 to the flanks of the second projection 24 and is hermetically attached to these projections. This results in a so-called air spring between the projections 23, 24 and hence also between the operating legs 3, 4. In this case, however, a problem is how to achieve a sufficient elasticity. In principle, the gap 20 can be filled also with some other highly yielding material, but most of these involve the difficulty of providing a sufficient sterility for operating room conditions. Therefore, the above-described clear opening is regarded at the moment as the best alternative. Even in the case that the spring element 7a, 7b is locked to the detector legs/operating legs by means of an axle 28, the projections 23, 24 are, at least over a length L2 of some profiled section, in a shape-matched gripping contact with the operating legs 3, 4. Thus, in all foregoing cases, the operating legs 3 and 4 are for example finger-pressable, such that the ends 8 of the spring element 7a–7d or the shaped length L2 thereof remain in a firm contact with the operating legs 3 and 4 without any bonding or other unreliable attachment. As already pointed out above, in addition to this shape-based contact, as an optional or concurrent way of achieving a gripping of the spring element 7 on the operating legs 3, 4 it is possible to use not necessarily a shape-matching locking with a length equal to the shaped length L2, but merely a shape-matching contact, especially when the spring element 7a, 7b surrounds the axis line 13 and the spring element is penetrated by the mechanical axle 28, as conceivable by means of FIGS. 3–4 and FIGS. 7A–7B. On the other hand, FIGS. 5 and 6 illustrate a shape-matched locking, wherein the ends 8 of the spring element extend through apertures in the operating legs 3, 4, such that there is no relative movement therebetween upon pressing or releasing the operating legs 3, 4 but that they remain immobile relative to each other, whereby, over a distance H3 therebetween, the spring element 7c, 7d remains immobile and and, over this distance H3, the spring element 7 is capable of functioning as a spring element.

As shown in FIGS. 3–6, the spring element 7a–7d is, in the direction of the operating legs, i.e. in a section parallel to the operating legs 3, 4, substantially V-shaped or U-shaped, the difference between these two concepts depending of course on the curvature of legs 23 and 24 or, respectively, surfaces 21 or 22 and/or on the radius of curvature of an angle therebetween and/or on an angle α therebetween. For the sake of simplicity, however, this application generally uses the concept V-shape, no matter what the curvatures or angles are. FIGS. 5 and 6 illustrate an embodiment, wherein the apex of a V-shape is provided with a free end 16 extending to the axial line 13 or falling short thereof by a length L3. Hence, in this case, the axle 28 does not extend through any member of the spring element 7 but externally thereof, as conceivable by means of FIGS. 5 and 6. FIGS. 3 and 4 illustrate an optional embodiment, wherein the apex of a V-shape is provided with a cylindrical type of portion 17 surrounding the axial line 13, as depicted also in FIGS. 7A and 7B. In each case, the legs 23, 24 of a V-shape extend either substantially along the operating legs 3, 4, as in FIGS. 3 and 4, or substantially towards the operating legs 3, 4, as in FIGS. 5 and 6. The locked immobilization of the spring element 7 can be effected according to the invention essentially by using two different methods, as already discussed above.

First of all, the spring element 7a, 7b can be locked in position by means of the axle 28 extending through the cylindrical type of portion 17 and the relatively overlapping area R of the detector legs 1, 2 and operating legs 3, 4, as shown in FIGS. 3 and 4 as well as 7A and 7B. Thus, the axle 28 keeps the spring element 7 absolutely immobile relative to the pairs of detector legs and operating legs. FIG. 7B illustrates an embodiment, wherein this axle 28 extends within said overlapping area R directly through the material of the spring element 7a, 7b. According to present understanding, however, it is more preferred to provide, as depicted in FIG. 7A, the axial hole of the spring element 7a, 7b with a bushing 38, which is in a non-rotatable contact with the spring element, whereby the actual pivoting element 5 and angular variations P1→M caused thereby as well as a bearing structure casing the pressure P2 are constituted between this bushing 38 and the axle 28 in relation to the detector legs and operating legs. This structure is depicted in FIG. 7A. This way, frictions and necessary forces are made as minute as possible. Optionally, the spring element 7c, 7d is immobilized solely by means of a mechanical shaped gripping contact between the relatively diverging ends 8 of the V-shaped spring element and the operating legs 3, 4, said spring element 7c, 7d being provided with a length extending through apertures in the legs 3, 4 and, at least one side thereof, and typically on both sides thereof, with a length expanding in any direction from the aperture, as conceivable by means of FIGS. 5 and 6. Thus, the ends 8 of the spring element 7c, 7d are not able to move relative to the operating legs 3, 4, but remain stationary relative thereto, whether the question is about the pressure P1 causing the opening M of the detector legs 1, 2 or about an outward force P3 causing the compression P2 of the detector legs. Especially in this latter case, but also in the case that the spring element 7 extends to the area of the axis line 13, the pivoting elements can be provided not only by using a mechanically functioning, through-going axle 28 but also axial elements 29 constituting an apparent axis line 13, as depicted in FIG. 7C. In this case, a projection 41 of the detector leg 2 and the operating leg 4 and a projection 42 of the detector leg 1 and the operating leg 3 are overlapped so as to produce a directly functional bearing therebetween. This is effected for example in such a way that the aperture of the projecting leg 41 is arranged pivotably between the projection of the leg 42 and the projection jacket, as shown in detail in FIG. 7C.

As for its width W2 substantially parallel to the axial line 13, the spring element 7 of the invention is at least 50% of, preferably at least 80% of, and typically roughly or substantially equal to the width W1 of the operating legs 3, 4 in this direction. Hence, the spring element 7 fills the space between the operating legs 3, 4 and has no inclination to pivoting. This does not mean that the cross-section of the spring element 7 in the direction of the axial line 13 could not be variable, which embodiment has not been shown in the figures, however. A consequence of this is that, in the case of FIGS. 5 and 6, the legs 23 and/or 24 may include holes or slots which are circumferential, transverse to that, or passing through the legs 23, 24. It should also be appreciated that the cylindrical portion or length 17 can be not only a segment of the circular cylinder but also, as studied in a cross-section, angular, corrugated, star-shaped etc. in terms of its outer surface.

According to the invention, the angle α between the converging surfaces 21 and 22 of the V-shaped legs of the spring element 7 is within the range of 70°–100°, preferably within the range of 80°–90°. A typical reading for the angle α can be for example in the order of 85°. When using a material of the same hardness for the spring element 7, the compressive force P2 of the detector legs can be reduced according to the invention by using a wider angle α between the surfaces 21, 22 and, if an increased compressive force P2 is desired, it is possible to use a narrower angle between the surfaces 21, 22. This way, the desired spring force or compressive force P2, which is applied to a finger, a toe, an ear, a nostril, or some other piece 6 of living tissue, whose characteristics are to be examined, can be set accurately as desired by properly dimensioning the angle α. Especially, when the angle α is relatively narrow and/or the spring element includes the length 17 surrounding the axial line 13, it can be said that the legs 23, 24 of the spring element 7 extend along the operating legs, as in FIGS. 3 and 4, and while the angle α is relatively wide and/or the spring element lies outside the axis line 13, it can be said that the legs 23, 24 of the spring element 7 extend towards the operating legs, as in FIGS. 5 and 6.

FIGS. 3, 5, and 6 illustrate such embodiments of the invention, wherein the spring element 7a, 7c, and 7d comprises a measuring sensor component, which is separate from and independent of cushions or casings 25a, 25b present on the converging surfaces of the operating legs. Thus, the casings 25a, 25b providing a cushioning and the spring element 7a, 7c, 7d can be made of different materials and can be designed very much independently of each other, which is beneficial. On the other hand, the number of components exceeds that used in the alternative embodiment of the invention. One preferred special embodiment of the invention is that the material of the spring element 7 extends, as for the length of the operating legs 3, 4, as an uninterrupted extension past the axial line 13 over to the length of the detector legs 1, 2, as shown in FIGS. 4 and 9A, 9B. These extensions 27a, 27b are flanked casings 25a, 25b exactly the same way as the casings 25a, 25b in the embodiments of FIGS. 3, 5, and 6, which do not relate to extensions but to components independent of the spring element.

Regardless of whether the casing 25a, 25b is integral or not with the spring element 7, the shape of said casing or cushion coming in contact with an object of measurement is adapted at a predetermined accuracy to match an outer shape 36a, 36b of the living tissue 6 to be measured. As a result of its flanks 26, this casing 25a, 25b sets at a distance S, required of a cushion, from the rigid structure of the detector leg 3, 4. This distance or space S can of course be also established by compiling the casing 25a, 25b e.g. from a solid-cell material, having a thickness which matches the desired cushion thickness. This embodiment, wherein the spring element and the cushion casings constituted by the extensions 27a, 27b are made in one and the same piece, is preferred in the sense that all components of a measuring sensor consisting of elastomer material can be manufactured for example in a single piece of casting or polymerization. FIG. 9A illustrates a combined spring element and casings manufactured in a single piece roughly in the position in which those have been molded or allowed to polymerize. Such a relative straight-component mold technique is advantageous. From this configuration, the combined spring element and casings are folded, in this case around the midpoint of the legs 23, 24 of the spring element 7 so as to produce a structure as shown in FIG. 9B, which in this condition is fitted between the detector legs 1, 2 and the operating legs 3, 4, on the mutually facing sides thereof. With minor exceptions, this results in a measuring sensor as shown in FIG. 4. The axis line 13 forms adjacent to the main folding point of the spring element-casing combination, as conceivable from FIGS. 9A and 9B. The cushion is formed by means of the distance S in such a manner that, as a result of the pressure force P2, the flanks 26 and the casings 25a, 25b resiliently yield in a desired fashion against a finger, a toe, ear surfaces, nostril surfaces, or some other such organ. The compatibility of the shapes of the casing 25a, 25b and the outer surfaces 36a, 36b of the piece 6 of living tissue to be examined secures a surface pressure as uniform as possible, the immobility of a measuring sensor, and a convenient use, especially on top of narrow and round extremities of the body. When the casings are made of a sufficiently soft material, a measuring sensor of the invention designed and dimensioned in view of fingers and/or toes can be mounted without any problems also on an ear lobe and a nasal septum. This results from the fact that, when studied from the outside, the casings 25a, 25b are in this case concave and very soft, a shape which adapts conveniently also to the shape of an ear lobe and a nasal septum, having a nearly uniform thickness. Depending on the material of the extensions 27a, 27b and hence possibly on the material of the spring element 7, according to whether these are made in a single piece or in separate pieces, as described above, the radiation or some other signal received by the detector elements may travel through the casings 25a, 25b, as shown in FIG. 6, or through the aperture 30 present therein, as in FIGS. 3–5. Respectively, the radiation or some other signal transmitted by the emission elements 12 may travel either through the material of the casings 25a, 25b of the detector legs, as shown in FIG. 6, or, alternatively, through the aperture 30 present in the material, as shown in FIGS. 3–5. In a prior known manner, the radiation or some other signal can be introduced into the living tissue 6 to be measured from a source present in the measuring sensor 10 itself or along a conductor 31 extending to the measuring sensor and containing a cable 43 or 45, and the radiation or some other signal is received from the living tissue to be measured in a detector included in the measuring sensor 10 itself or, alternatively, along a conductor 32 extending from the detector and containing a cable 44 or 45. In case the emission source and the detector are included in the measuring sensor 10 itself, said conductors are electrical wires, suitable for some applications, but in several cases the conductors 31 and 32 are light conductors, such as optical cables, whereby the actual signal receivers and emission sources are located outside the actual measuring sensor 10, such as in a surveillance monitor.

In a structure of the invention, the spring element, i.e. the spring element 7a–7d, is constituted by an elastomer material having resilient properties at operating temperature. Thus, the question is about a material which is not a metal or a metal alloy or any other material receiving or conducting a magnetic field or electrical field or electric current. Hence, the elastomer material consists of a polymer whose macro-molecular chains are cross-linked to each other. Preferably, the spring element 7 is constituted by silicone rubber or some other synthetic or natural rubber, as elastomer materials are commonly called, or possibly by polyurethane or the like. Preferably, the spring element is constituted by hot-cured silicone rubber, having a hardness range of 20–40 or optionally 50–70 Shore A. In other words, it is possible to use either distinctly softer silicone rubber or reasonably hard silicone rubber, according to which of course, as described above, is dimensioned the angle α between the mutually facing surfaces 21, 22 of the V-shaped legs, and of course the thickness and other design of the legs. Preferably, the spring element 7 has a hardness range of 25–35 or optionally 55–65 Shore A. In addition to the design, it is understandable that, for a lesser pressure force P2, use is typically made of elastomer softer than these and, for a more powerful pressure force P2, use is typically made of harder elastomer. In this connection, it should be kept in mind, however, that the compressive or pressure force P2 is a combined effect, resulting not only from the hardness of elastomer but also from the dimensioning of the spring element 7. In any case, the pressure force P2 caused by the spring element 7 of the invention remains very well constant by using a predetermined dimensioning and predetermined hardness.

As already indicated above, a described type of measuring sensor can be used for investigating non-invasively characteristics of any piece 6 of living tissue, such as a finger, a toe, an ear lobe, a nasal septum etc., on the basis of a change in completely transmitting or partially transmitting and reflecting electromagnetic waves. A completely transmitting system is depicted in FIGS. 4–6, while FIG. 3 illustrates both a solely detecting system and a system, wherein the electromagnetic waves are applied to the piece 6 of living tissue from a given direction D1 and the radiation reflecting into the tissue and back therefrom in a direction D2 is detected on the same side of an object of measurement. Typically, and especially in the case of pulseoximetry, the electromagnetic waves comprise infrared radiation and radiation close to it. Thus, the measurement is directed for example to the characteristics of blood, such as its composition or some characteristic, such as oxygen saturation of a blood component.

What is claimed is:
1. A measuring sensor (10) for measuring characteristics of living tissue in a living body extremity, the measuring sensor comprising:
   a. at least two rigid detector legs (1, 2) movable (P1→M) to varying distances (H1 . . . H2) from each other,
   b. a detector means (11) positioned on at least one of the detector leg;
   c. an emission means (12) positioned on at least one of the detector legs, the emission means and the detector means being arranged such that the detector means receives a signal emitted by the emission means;
   d. pivoting elements (5) formed in the detector legs, the pivoting elements connecting the detector legs and forming a pivot axis line (13) about which the detector legs are movable relative to each other;
   e. at least two rigid operating legs (3, 4) each having a total length (L1) extending between a first end and an outer end, the first end of each operating leg being attached to one of the detector legs, the outer end of each operating leg extending beyond the pivot axis line (13); and f. a spring element (7) positioned between the operating legs for producing a compressive force (P2) between the detector legs when the living tissue is positioned between the detector legs, the spring element being composed of a resilient elastomer material, wherein the spring element includes a solid body continuously extending from the first rigid operating leg to the second rigid operating leg, the spring element being in gripping contact with both the first operating leg and the second operating leg over a first length (L2) that is located substantially on the total length (L1) of the respective operating leg between the pivot axis line and the outer end of each operating leg;

wherein the spring element is shaped such that the pivot axis line extends through the spring element, the spring element including projections (23, 24) directed from the pivot axis line toward the outer end of the respective operating leg, the projections having a gap (20) therebetween at least substantially open to surrounding atmosphere, the projections being in gripping contact with the respective operating leg.

2. A measuring sensor of claim 1, wherein the spring element is an uninterupted member extending from the outer ends of each operating leg to the pivot axis line, the spring element further including a pair of opposed ends (8), the pair of opposed ends being spaced apart from each other by a distance perpendicular to the pivot axis line, each end of the spring element being locked with a shape-matched contact to the respective operating leg (3, 4).

3. The measuring sensor of claim 2 wherein the spring element includes an outer surface extending between the pair of opposed ends, the outer surface of the spring element being concave relative to the direction of the axis line.

4. The measuring sensor of claim 2 wherein the spring element includes an outer surface extending bet ween the pair of opposed ends, the outer surface of the spring element being convex relative to the direction of the axis line.

5. The measuring sensor of claim 2 wherein the spring element has its apex provided with a free end (16).

6. The measuring sensor of claim 1 wherein the spring element is substantially V-shaped having a pair of mutual facing surfaces, the V-shape having its apex positioned to surround the pivot axis line.

7. The measuring sensor of claim 6 wherein an angle ($\alpha$) is formed between the mutual facing surfaces of the V-shaped spring element, the angle being in the range of 70°–100°.

8. The measuring sensor of claim 7 wherein the angle is in the range of 80°–90°.

9. The measuring sensor of claim 1, wherein the spring element has a width (W2) that is at least 50% of the width (W1) of the operating leg in the direction of the pivot axis line.

10. The measuring sensor of claim 1 wherein the spring element has a width (W2) that is at least 80% of the width (W1) of the operating leg in the direction of the pivot axis line.

11. The measuring sensor of claim 1, wherein the spring element has a width (W2) that is at is substantially equal to the width (W1) of the operating leg in the direction of the pivot axis line.

12. The measuring sensor of claim 1 wherein the detector means and the emmission means are arranged on the detector legs so as to non-invasively measure a characteristic of the living tissue on the basis of a change in electromagnetic waves passing through living tissue positioned between the detector legs.

13. The measuring sensor of claim 12 wherein the electromagnetic waves include infrared radiation and the measuring sensor is adapted to measure the charateristics of blood passing through the living tissue.

14. The measuring sensor of claim 12 wherein the detector means and emission means are arranged to measure the characteristics of living tissue with transmitting, or patially transmitting and reflecting radiation.

15. The measuring sensor of claim 1 wherein the measuring sensor is adapted for pulseoximetric measurements.

16. The measuring sensor of claim 1 where the detection means and the emission means in the detector legs comprise conductors, which are light conductors.

17. A measuring sensor (10) for measuring characteristics of living tissue in a living body extremity, the measuring sensor comprising;

a. at least two rigid detector legs (1, 2) movable (P1→M) to varying distances (H1 . . . H2) from each other;

b. a detector means (11) positioned on at least one of the detector legs;

c. an emission means (12) positioned on at least one of the detector legs, the emission means and the detector means being arranged such that the detector means receives a signal emitted by the emission means;

d. pivoting elements (5) formed in the detector legs, the pivoting elements connecting the detector legs and forming a pivot axis line (13) about which the detector legs are movable relative to each other;

e. at least two rigid operating legs (3, 4) each having a total length (L1) extending between a first end and an outer end, the first end of each operating leg being attached to one of the detector legs, the outer end of each operating leg extending beyond the pivot axis line (13); and f. a spring element (7) positioned between the operating legs for producing a compressive force (P2) between the detector legs when the living tissue is positioned between the detector legs, the spring element being composed of a resilient elastomer material, wherein the spring element includes a solid body continuously extending from the first rigid operating leg to the second rigid operating leg, the spring element being in gripping contact with both the first operating leg and the second operating leg over a first length (L2) that is located substantially on the total length (L1) of the respective operating leg between the pivot axis line and the outer end of each operating leg;

wherein the spring element includes an aperture extending therethrough, the aperture extending concentrically with the pivot axis line, the aperture receiving an axle (28) connected to the pivot elements of each detector leg to provide pivoting movement between the detector legs.

18. A measuring sensor (10) for measuring characteristics of living tissue in a living body extremity, the measuring sensor comprising:

a. at least two rigid detector legs (1, 2) movable (P1→M) to varying distances (H1 . . . H2) from each other;

b. a detector means (11) positioned at least one of the detector legs;

c. an emission means (12) positioned on at least one of the detector legs, the emission means and the detector means being arranged such that the detector means receives a signal emitted by the emission means;

d. pivoting elements (5) formed in the detector legs, the pivoting elements connecting the detector legs and forming a pivot axis line (13) about which the detector legs are movable relative to each other;

e. at least two rigid operating legs (3, 4) each having a total length (L1) extending between a first end and an outer end, the first end of each operating leg being attached to one of the detector legs, the outer end of each operating leg extending beyond the pivot axis line (13); and f. a spring element (7) positioned between the operating legs for producing a compressive force (P2) between the detector legs when the living tissue is positioned between the detector legs, the spring element being composed of a resilient elastomer material, wherein the spring element includes a solid body continuously extending from the first rigid operating leg to the second rigid operating leg, the spring element being in gripping contact with both the first operating leg and the second operating leg over a first length (L2) that is located substantially on the total length (L1) of the respective operating leg between the pivot axis line and the outer end of each operating leg;

wherein the spring element is formed from a cross-linked polymer having macro-molecular chains consisting of silicon or carbon.

19. The measuring sensor of claim 18 wherein the spring element is formed from hot-cured silicon rubber having a hardness range of 20–40 shore A.

20. The measuring sensor of claim 18 wherein the spring element is formed from hot-cured silicon rubber having a hardness range of 50–70 shore A.

21. A measuring sensor (10) for measuring characteristics of living tissue in a living body extremity, the measuring sensor comprising:

a. at least two rigid detector legs (1, 2) movable (P1→M) to varying distances (H1 . . . H2) from each other;

b. a detector means (11) positioned on at least one of the detector legs;

c. an emission means (12) positioned on at least one of the detector legs, the emission means and the detector means being arranged such that the detector means receives a signal emitted by the emission means;

d. pivoting elements (5) formed in the detector legs, the pivoting elements connecting the detector legs and forming a pivot axis line (13) about which the detector legs are movable relative to each other;

e. at least two rigid operating legs (3, 4) each having a total length (L1) extending between a first end and an outer end, the first end of each operating leg being attached to one of the detector legs, the outer end of each operating leg extending beyond the pivot axis line (13); and f. a spring element (7) positioned between the operating legs for producing a compressive force (P2) between the detector legs when the living tissue is positioned between the detector legs, the spring element being composed of a resilient elastomer material, wherein the spring element includes a solid body continuously extending from the first rigid operating leg to the second rigid operating leg, the spring element being in gripping contact with both the first operating leg and the second operating leg over a first length (L2) that is located substantially on the total length (L1) of the respective operating leg between the pivot axis line and the outer end of each operating leg;

wherein the spring element includes a casing (25a; 25b) that extends past the pivot axis line onto the detector legs, the casing having an outer shape generally corresponding to the living tissue to be measured.

22. The measuring sensor of claim 21 wherein the casing is provided with flanks (26) setting a cushioning distance (S) apart from the rigid operating legs.

23. The measuring sensor of claim 21 wherein the signal received by the detector means and the radiation transmitted by the emission means passes through the material of the casing.

24. The measuring sensor of claim 21 wherein the signal received by the detector means and the signal transmitted by the emission means passes through an aperture formed in the casing.

25. A measuring sensor (10) for measuring characteristics of living tissue in a living body extremity, the measuring sensor comprising:

a. at least two rigid detector legs (1, 2) movable (P1→M) to varying distances (H1 . . . H2) from each other;

b. a detector means (11) positioned on at least one of the detector legs;

c. an emission means (12) positioned on at least one of the detector legs, the emission means and the detector means being arranged such that the detector means receives a signal emitted by the emission means;

d. pivoting elements (5) formed in the detector legs, the pivoting elements connecting the detector legs and forming a pivot axis line (13) about which the detector legs are movable relative to each other;

e. at least two rigid operating legs (3, 4) each having a total length (L1) extending between a first end and an outer end, the first end of each operating leg being attached to one of the detector legs, the outer end of each operating leg extending beyond the pivot axis line (13); and f. a spring element (7) positioned between the operating legs for producing a compressive force (P2) between the detector legs when the living tissue is positioned between the detector legs, the spring element being composed of a resilient elastomer material, wherein the spring element includes a solid body continuously extending from the first rigid operating leg to the second rigid operating leg, the spring element being in gripping contact with both the first operating leg and the second operating leg over a first length (L2) that is located substantially on the total length (L1) of the respective operating leg between the pivot axis line and the outer end of each operating leg;

wherein the spring element is substantially V-shaped having a pair of mutually facing surfaces with an angle ($\alpha$) therebetween to provide a predetermined spring force.

26. A measuring sensor (10) for measuring characteristics of living tissue in a living body extremity, the measuring sensor comprising:

a. at least two rigid detector legs (1, 2) movable (P1→M) to varying distances (H1 . . . H2) from each other;

b. a detector means (11) positioned on at least one of the detector legs;

c. an emission means (12) positioned on at least one of the detector legs, the emission means and the detector means being arranged such that the detector means receives a signal emitted by the emission means;

d. pivoting elements (5) formed in the detector legs, the pivoting elements connecting the detector legs and forming a pivot axis line (13) about which the detector legs are movable relative to each other;

e. at least two rigid operating legs (3, 4) each having a total length (L1) extending between a first end and an outer end, the first end of each operating leg being attached to one of the detector legs, the outer end of each operating leg extending beyond the pivot axis line (13);

f. a spring element (7) positioned between the operating legs for producing a compressive force (P2) between the detector legs when the living tissue is positioned between the detector legs, the spring element being composed of a resilient elastomer material, wherein the spring element includes a solid body continuously extending from the first rigid operating leg to the second rigid operating leg, the spring element being in gripping contact with both the first operating leg and the second operating leg over a first length (L2) that is located substantially on the total length (L1) of the respective operating leg between the pivot axis line and the outer end of each operating leg; and g. projections formed on each of the detector legs and an axle (28) extending between the projections formed on each of the detector legs, the axle extending through the spring element to immobilize the spring element.

27. A measuring sensor (10) for measuring characteristics of living tissue in a living body extremity, the measuring sensor comprising:

a. at least two rigid detector legs (1, 2) movable (P1→M) to varying distances (H1 . . . H2) from each other;

b. a detector means (11) positioned on at least one of the detector legs;

c. an emission means (12) positioned on at least one of the detector legs, the emission means and the detector means being arranged such that the detector means receives a signal emitted by the emission means;

d. pivoting elements (5) formed in the detector legs, the pivoting elements connecting the detector legs and forming a pivot axis line (13) about which the detector legs are movable relative to each other;

e. at least two rigid operating legs (3, 4) each having a total length (L1) extending between a first end and an outer end, the first end of each operating leg being attached to one of the detector legs, the outer end of each operating leg extending beyond the pivot axis line (13);

f. a spring element (7) positioned between the operating legs for producing a compressive force (P2) between the detector legs when the living tissue is positioned between the detector legs, the spring element being composed of a resilient elastomer material, wherein the spring element includes a solid body continuously extending from the first rigid operating leg to the second rigid operating leg, the spring element being in gripping contact with both the first operating leg and the second operating leg over a first length (L2) that is located substantially on the total length (L1) of the respective operating leg between the pivot axis line and the outer end of each operating leg; and g. projections formed on each of the detector legs, the projections being coupled to each other with mutual apertures and jackets within their overlapping area (R) to form the pivot axis line.

28. The measuring sensor of claim 27 wherein the spring element includes an outer surface extending between a pair of opposed ends (8), the outer surface of the spring element being concave relative to the direction of the axis line.

29. The measuring sensor of claim 27 wherein the spring element includes an outer surface extending between a pair of opposed ends (8), the outer surface of the spring element being convex relative to the direction of the axis line.

30. The measuring sensor of claim 27 wherein the spring element has its apex provided with a free end (16).

31. The measuring sensor of claim 27 wherein the detector means and emission means are arranged such that the emission means transmits radiation and the detector means measures reflected radiation to measure the characteristics of living tissue.

32. The measuring sensor of claim 27 wherein the measuring sensor is adapted for pulseoximetric measurements.

33. The measuring sensor of claim 27 wherein the detection means and the emission means in the detector legs comprise conductors, which are light conductors.

34. A measuring sensor for measuring characteristics of living tissue in a living body extremity, the measuring sensor comprising:

a pair of detector legs (1, 2) formed to receive the living body extremity therebetween, each detector leg including a pair of opposed, depending projections (5), the projections being coupled to each other to define a pivot axis line (13) about which the detector legs are movable with respect to each other;

a detector means (11) positioned on one of the detector legs;

an emission means (12) positioned on one of the detector legs, wherein the emission means emits a signal through the living body extremity, said signal being detected by the detector means;

a pair of rigid operating legs (3, 4) each attached to one of the detector legs and extending from the detector leg on an opposite side of the pivot axis line; and a spring element (7) positioned between the operating legs to produce a compressive force to urge the operating legs away from each other and the detector legs toward each other, the spring element including a pair of resilient projections (23, 24) extending at an angle (α) relative to each other, each projection being in gripping contact with one of the operating legs, wherein the angle decreases when the operating legs are moved toward each other.

35. The measuring sensor of claim 34 wherein each operating leg is integrally formed with one of the detector legs and the spring element is formed independently from the detector legs and operating legs.

36. The measuring sensor of claim 34 wherein the spring element is formed from hot-cured silicon rubber having a hardness range of 20–40 shore A.

37. The measuring sensor of claim 34 wherein the spring element is formed from hot-cured silicon rubber having a hardness range of 50–70 shore A.

38. The measuring sensor of claim 34 wherein an angle (α) is formed between the mutual facing surfaces of the V-shaped spring element, the angle being in the range of 70°–100°.

39. The measuring sensor of claim 38 wherein the angle is in the range of 80°–90°.

40. The measuring sensor of claim 34 wherein the detector means and the emitter means are arranged on the detector legs so as to non-invasively measure a characteristic of the living tissue on the basis of a change in electromagnetic waves passing through living tissue positioned between the detector legs, the electromagnetic waves including infrared radiation and the measuring sensor is adapted to measure the characteristics of blood passing through the living tissue.

41. The measuring sensor of claim 34 wherein the measuring sensor is adapted for pulseoximetric measurements.

42. The measuring sensor of claim 34 wherein the spring element includes a casing (25a; 25b) that extends past the pivot axis line onto the detector legs, the casing having an outer shape generally corresponding to the living tissue to be measured.

43. The measuring sensor of claim 21 wherein the signal received by the detector means and the radiation transmitted by the emission means passes through the material of the casing.

44. The measuring sensor of claim 34 wherein the detection means and the emission means in the detector legs comprise conductors, which are light conductors.

45. A measuring sensor for measuring characteristics of living tissue in a living body extremity, the measuring sensor comprising:

a pair of detector legs (1, 2) formed to receive the living body extremity therebetween, each detector leg including a pair or opposed, depending pivot elements (5), the pivot elements being coupled to each other to define a pivot axis line (13) about which the detector legs are movable with respect to each other;

detector means (11) positioned on one of the detector legs;

emission means (12) positioned on one of the detector legs, wherein the emission means emits a signal through the living body extremity, said signal being detected by the detector means;

a pair of rigid operating legs (3, 4) each attached to one of the detector legs and extending from the detector leg on an opposite side of the pivot axis line; and a spring element (7) positioned between the operating legs to produce a compressive force to urge the operating legs away from each other and the detector legs toward each other, the spring element being substantially V-shaped having a pair of resilient projections (23, 24) extending at an angle (α) relative to each other and a gap (20) therebetween at least substantially open to surrounding atmosphere, each projection being in gripping contact with one of the operating legs, wherein the angle decreases when the operating legs are moved toward each other.

46. The measuring sensor of claim 45, wherein the spring element includes at least one outer surface (14a and/or 14b) substantially parallel to the pivot axis line, the outer surface being concave.

47. The measuring sensor of claim 45, wherein the spring element includes at least one outer surface (14a and/or 14b) substantially parallel to the pivot axis line, the outer surface being convex.

48. The measuring sensor of claim 45, wherein the spring element (7a, 7b) extends within the area of said pivot axis line (13) around this axis line, and the projections (23, 24) having a shaped length (L2) providing said gripping contact with the operating legs.

49. The measuring sensor of claim 45, wherein the spring element (7) is immobilized by means of an axle (28) extending through a cylindrical portion (17) of the spring element.

50. The measuring sensor of claim 45, wherein the spring element (7) is formed from a cross-linked polymer whose macro-molecular chains consist of silicon or carbon, being within a hardness range of 20–40 Shore A or 55–65 Shore A, whereupon a minor spring force is obtained by using a softer of said elastomers and a major spring force is obtained by using a harder of said elastomers.

51. The measuring sensor of claim 45, wherein the angle (α) between the mutually facing surfaces (21, 22) of the V-shaped spring element (7) is within the range of 70°–100°, whereupon a predetermined minor spring force is obtained by using a wider angle and a predetermined major spring force is obtained by using a smaller angle.

52. The measuring sensor of claim 45, wherein said detection means and said emission means in the detector legs comprise conductors, which are light conductors.

53. The measuring sensor of claim 45, wherein the detector means and emission means are arranged to measure the characteristics of blood with transmitting, or partially transmitting and reflecting radiation.

54. The measuring sensor of claim 45, wherein the spring element (7) is immobilized by means of axle elements (29) in an overlapping area ® of the detector legs and the operating legs.

* * * * *